United States Patent [19]

Occelli et al.

[11] Patent Number: 4,788,186

[45] Date of Patent: Nov. 29, 1988

[54] 6-SUBSTITUTED-S-TRIAZOLO[3,4-A]PHTHALAZINE DERIVATIVES

[75] Inventors: Emilio Occelli, Parabiago; Domenico Barone, Milan; Giorgio Tarzia, Milan; Adele Giunta, Milan, all of Italy

[73] Assignee: Gruppo Lepetit S.p.A., Gerenzano, Italy

[21] Appl. No.: 112,015

[22] Filed: Oct. 20, 1987

Related U.S. Application Data

[63] Continuation of Ser. No. 18,812, Feb. 20, 1987, abandoned, which is a continuation of Ser. No. 458,003, Jan. 14, 1983, abandoned.

[30] Foreign Application Priority Data

Jan. 18, 1982 [GB] United Kingdom ............... 8201273

[51] Int. Cl.$^4$ ............... A61K 31/535; A61K 31/50; C07D 487/04
[52] U.S. Cl. ............... 514/210; 514/248; 514/230.8; 514/232.5; 514/233.2; 544/81; 544/115; 544/234
[58] Field of Search ............... 544/81, 115, 234; 514/248, 228, 232, 233, 234, 236, 237, 239, 210

[56] References Cited

U.S. PATENT DOCUMENTS 2,484,029 10/1949 Hartmann et al. ............... 544/237

FOREIGN PATENT DOCUMENTS

| 29130 | 5/1981 | European Pat. Off. . |
| 51-032598 | 3/1976 | Japan . |
| 53-21197 | 2/1978 | Japan . |
| 629177 | 12/1946 | United Kingdom . |

OTHER PUBLICATIONS

Buzykin, et al., Khim. Geterotsikl. Soedin, (1978), No. 5, pp. 690–698.
Druey, et al., Helvetica Chimica Acta., vol. XXXIV, Fas. I (1951) No. 21, pp. 195–206.
Golik, J. Heterocyclic Chem., vol. 13, (1976), pp. 613–614.
Moroi, et al., Chem. Pharm. Bull., 24(11), (1976), pp. 2850–2856.
Potts, et al., J. Org. Chem., 34(11), (1969), pp. 3221–3230.
Sano, et al., Chem. Pharm. Bull., 22(12), (1974), pp. 3006–3009.
Twomey, Proc. Royal Irish Acad. Sci., 74, (1976), pp. 32–52.
Kac, et al., Chem. Abstracts, vol. 85, (1976), Entry 32958q.
Yurugi, et al., Chem. Abstracts, vol. 80, (1974), Entry 37056a.
Yurugi, et al., Chem. Abstracts, vol. 80 (1974), Entry 37073d.
U.S. Public Health Service Research Grant CA084-95-03, Mar. 1, 1968, pp. 1 and 6.
Buzykin, et al., *Chem. Abstracts,* vol. 83, (1975), p. 496 Abstract Number: 147445w.
Ivanova, et al., *Chem. Abstracts,* vol. 91, (1979), p. 591, Abstract Number: 29566d.
Golik, *Chem. Abstracts,* vol. 85, (1976), p. 521, Abstract Number: 143051h.
Chem. Abs. 3864t, vol. 81, 1974.
Chem. Abs. 146857u, vol. 89, 1978.
Castle: "Heterocyclic Compounds", vol. 27, pp. 631–638.
G. A. Reynolds, et al., J. Org. Chem., 24, 1205 (1959).
H. Zimmer, et al., J. Org. Chem., 40, 2901 (1975).
K. Ueno, et al., Chemical and Pharmaceutical Bulletin, 24(5), 1068 (1976).
Chemical Abstract Number 92:94311b abstracting D. Twomey, Proc. R. Ir. Acad., Sect. B 79B(3), 29 (1979).

*Primary Examiner*—Donald G. Daus
*Assistant Examiner*—William A. Teoli, Jr.
*Attorney, Agent, or Firm*—Stephen L. Nesbitt

[57] ABSTRACT

The present invention refers to new s-triazolo[3,4-a]phthalazine derivatives, to the process for their preparation and to the pharmaceutical compositions containing them.

29 Claims, No Drawings

6-SUBSTITUTED-S-TRIAZOLO[3,4-A]PHTHALAZINE DERIVATIVES

CROSS-REFERENCE TO RELATED APPLICATION

This is a continuation of application Ser. No. 018,812, filed Feb. 20, 1987, now abandoned, which is a continuation of application Ser. No. 458,003, filed Jan. 14, 1983, now abandoned.

The present invention refers to new s-triazolo[3,4-a]phthalazine derivatives, to the process for their preparation and to the pharmaceutical compositions containing them.

The new s-triazolo[3,4-a]phthalazines of the present invention are represented by the following general formula

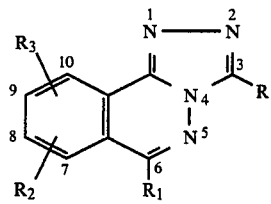

wherein
R represents hydrogen, hydroxy, $(C_1-C_6)$alkyl, phenyl, substituted phenyl, carbo-$(C_1-C_4)$alkoxy, chloro, mercapto, $(C_1-C_4)$alkylthio, $(C_1-C_4)$alkylsulfinyl, $(C_1-C_4)$alkylsulfonyl, an amino or substituted amino group of formula

wherein $R_4$ and $R_5$, each independently, represent hydrogen, $(C_1-C_4)$alkyl, $(C_2-C_4)$alkenyl, $(C_1-C_4)$alkyl substituted with one or two groups independently selected from hydroxy, $(C_1-C_4)$alkoxy, halogen, carboxy, cyano and aminocarbonyl, mono- or di-$(C_1-C_4)$alkylamino-carbonyl, $(C_1-C_4)$alkoxycarbonyl, $(C_1-C_4)$alkoxythiocarbonyl, $(C_1-C_4)$alkylthiocarbonyl, phenyl-$(C_1-C_4)$alkyl or substituted phenyl-$(C_1-C_4)$alkyl wherein the alkyl portion may be substituted as defined above, or $R_4$ and $R_5$ taken together with the adjacent nitrogen atom may represent a saturated 4, 5, 6, or 7-membered heterocyclic ring which may contain a further heteroatom selected from nitrogen, oxygen, and sulfur and optionally bear one or two substituents independently selected from $(C_1-C_4)$alkyl, phenyl, substituted phenyl, hydroxy, and carbo-$(C_1-C_4)$alkoxy, or R represents an alkoxy or cycloalkoxy group of formula —$OR_6$ wherein $R_6$ stands for a $(C_1-C_6)$alkyl substituted with one or two groups independently selected from hydroxy, amino, mono- or di-$(C_1-C_4)$alkylamino, $(C_1-C_4)$alkoxy, halogen, oxo, carboxy, aminocarbonyl, mono- or di-$(C_1-C_4)$alkylaminocarbonyl, and $(C_1-C_4)$-alkoxycarbonyl, $(C_1-C_4)$alkoxythiocarbonyl, and $(C_1-C_4)$alkylthiocarbonyl, or $R_6$ is a saturated 4, 5, 6, or 7-membered heterocyclic ring which may contain a further heteroatom selected from nitrogen, oxygen, and sulfur and optionally bear one or two substituents independently selected from $(C_1-C_4)$alkyl, phenyl, substituted phenyl, hydroxy, and carbo-$(C_1-C_4)$alkoxy, or $R_6$ is a $(C_5-C_8)$cycloalkyl group optionally substituted with one or more hydroxy and $(C_1-C_4)$alkoxy group;

$R_1$ is selected from halogen, hydroxy, $(C_1-C_4)$alkylthio, $(C_1-C_4)$alkylsulfinyl, $(C_1-C_4)$alkylsulfonyl, phenyl, substituted phenyl, an amino or substituted amino group of formula

wherein $R_7$ and $R_8$ are defined as above for $R_4$ and $R_5$, and an alkoxy or cycloalkoxy group of formula —$OR_9$ wherein $R_9$ is defined as $R_6$ above; and $R_2$ and $R_3$ each independently represent hydrogen, halogen, $(C_1-C_4)$alkyl, $(C_1-C_4)$alkoxy and nitro; with the proviso that when simultaneously $R_2$ and $R_3$ are hydrogen and $R_1$ is chloro, R must be different from phenyl or 4-nitrophenyl, and that when $R_1$ is hydroxy, R must be different from phenyl; with the further proviso that when R and/or $R_1$ are —O—$R_6$ or —$OR_9$, respectively, wherein $R_6$ and/or $R_9$ are a saturated heterocyclic ring as above defined, the heteroatom of said heterocycle cannot be directly linked to the oxygen atom.

A preferred group of compounds of the present invention, comprises those compounds of formula I wherein R is phenyl or substituted phenyl, $R_1$ is an amino or substituted amino group of formula

or an alkoxy or cycloalkoxy group of formula —$OR_9$ wherein $R_7$, $R_8$, and $R_9$ are as defined above, and $R_2$ and $R_3$ each independently represent hydrogen, halogen, $(C_1-C_4)$alkyl and $(C_1-C_4)$alkoxy.

As used herein the term "substituted phenyl" is intended to refer to a phenyl group wherein one, two or three hydrogens are replaced by groups each independently selected from $(C_1-C_6)$alkyl, $(C_1-C_6)$alkoxy, halogen, phenyl, hydroxy, amino, mono- and di-$(C_1-C_4)$alkylamino, $(C_2-C_4)$alkanoylamino, piperidino, cyano, nitro, trifluoromethyl, carboxy, and carbamyl. The terms "alkyl" or "alkoxy" per se as well as the alkyl or alkoxy portions in other substituents containing said moieties, designate straight or branched alkyl or alkoxy groups which contain a number of carbon atoms within the range specified, between parenthesis, before the term. Thus, for instance, the term "$(C_1-C_4)$alkyl" designates a straight or branched alkyl radical which may contain 1, 2, 3, or 4 carbon atoms. Finally, the term "halogen" identifies chloro, bromo, fluoro, and iodo.

The compounds of the present invention when tested in vitro in the benzodiazepine receptor binding test, showed to act selectively on the rat brain benzodiazepine receptors displacing $^3H$-diazepam from its specific receptors with a potency which, in some instances, is superior to that of benzodiazepines. Furthermore, the compounds of the present invention showed to be able to displace $^3H$-diazepam from its specific brain receptors also when tested in vivo. This activity on benzodiazepine receptors is known to reflect, and actually reflects, an antianxiety activity which is detectable in animals by the pharmacological tests usually employed in this field. Said activity is of particular interest in that at the effective doses tested, it is not accompanied by the side effects typically associated to benzodiazepines, such as sedation, motor incohordination, etc.

The s-triazolo[3,4-a]phthalazine ring system was first reported in literature in 1951 when J. Druey and B. H. Ringier Helvetica Chimica Acta 34, 195, described the synthesis and the chemico-physical characteristics of a series of s-triazolo[3,4-a]phthalazines. Since then, the study of this new ring system developed considerably, leading to the synthesis of several other s-triazolo[3,4-a]phthalazine derivatives, with interest being directed essentially toward their antihypertensive properties (see for instance Chem. Abstracts 80, 37056 a, (1974) and Dissertation Abstr. Intern. B 32, No. 7, 3859 (1972)). This study was further stimulated by the identification of metabolites of hydralazine and budralazine having a triazolo-phthalazine structure (see Arzneimittel - Forsch., 1977, II, 27, 2388-95; Chem. Pharm. Bull. 22, No. 12, 3006-09 (1974) and Chem. Pharm. Bull. 24, No. 11, 2850-58 (1976)). Furthermore several other triazolo[3,4-a]phthalazines have been synthetized up to now, having a different pharmacological activity and more particularly active as antiinflammatories (see for instance Japanese Patent Application No. 104949/74, Kokai No. 51/032598 (Derwent:Farmdoc 33086X)), with anticancer activity (see Chem. Abstr. 81, 3864 t, 1974) and with bronchodilating activity (see Chem. Abstr. 80, 37073 d, (1974)).

A general method for preparing the compounds of the present invention consists in cyclizing a 4-substituted-1-hydrazino-phthalazine of formula II

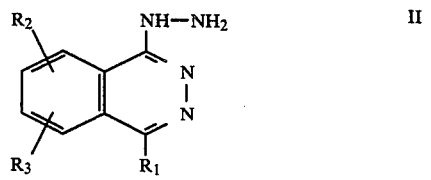

wherein $R_1$, $R_2$, and $R_3$ are as defined before, with a suitable cyclizing agent and optionally transforming the substituent at the 3-position of the triazolo[3,4-a]phthalazine nucleus according to common procedures. More particularly, compounds of formula I wherein R is $(C_1-C_6)$alkyl, phenyl, substituted phenyl, or carbo-$(C_1-C_4)$-alkoxy, are conveniently prepared by reacting the 4-substituted-1-hydrazino-phthalazine II with an acid derivative of the formula

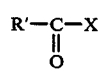

wherein R′ stands for $(C_1-C_6)$alkyl, phenyl, substituted phenyl or carbo-$(C_1-C_4)$alkoxy, and X stands for a chlorine atom, or a group —OR″ wherein R″ is methyl, ethyl, the same group

trifluoroacetyl or ethoxycarbonyl.

The reaction is advantageously conducted in an inert organic solvent and in the presence of a tertiary organic nitrogen base which blocks the organic or inorganic acid which forms during the course of the reaction. Suitable solvents include dioxane, tetrahydrofuran, and lower aliphatic halogenated and aromatic hydrocarbons. Suitable tertiary organic nitrogen bases that may be employed include trialkylamines, pyridine, pycolines and the like. The reaction can be conducted at a temperature range of from room temperature to the reflux temperature of the reaction mixture, for a period of time that depends on the reactants employed and the temperature at which the reaction is carried out. In general the reaction is conducted by adding a solution of an equimolar amount or preferably a slight excess of the acid derivative to a solution of the 4-substituted 1-hydrazinophthalazine derivative of formula II and then heating the reaction mixture to the reflux temperature for a period of time ranging from about 2 to about 12 hours.

The desired products so obtained are isolated and purified using standard isolation and purification techniques well known to those skilled in the art. Thus, for example, the reaction mixture is cooled, the reaction solvent is evaporated off, the residue is washed with a small amount of water and finally crystallized from a suitable crystallization solvent.

Compounds I wherein R is hydrogen are easily obtained by using as the cyclizing agent a trialkyl orthoformate, while compounds I wherein R is a mercapto group are prepared by cyclizing a 1-hydrazinophthalazine II with carbon disulfide in the presence of aqueous sodium hydroxide or in chloroform. Once a compound I is obtained wherein R is a mercapto group, it can be easily transformed into the corresponding compound I wherein R is chloro by oxidative chlorination, e.g. by passing a chlorine stream into a solution of the triazolo[3,4-a]phthalazine-3-thiolo in water/chloroform cooled to low temperature.

The 3-chloro substituent thus introduced undergoes displacement by amines of formula

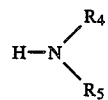

or alkali metal alkoxides or cycloalkoxides of formula $MeOR_6$ wherein Me is an alkali metal cation, forming the corresponding compounds I wherein R is an amino group

or an alkoxy or cycloalkoxy group of formula $OR_6$ wherein $R_4$, $R_5$, and $R_6$ are as defined before.

In particular, this displacement reaction is conveniently carried out by refluxing a 3-chloro-triazolo[3,4-a]phthalazine derivative with at least an equimolar amount, but preferably an excess, of the suitably selected amine $HNR_4R_5$ or alkoxide $MeOR_6$. When the amine $HNR_4R_5$ is employed, the use of an organic solvent may sometimes be avoided using an excess of the amine itself, while when the alkoxide $MeOR_6$ is employed, an organic solvent which does not interfere with the reaction course is necessary. Suitable solvents are for instance lower aliphatic alcohols, glycols, and their lower alkyl ethers, dioxane tetrahydrofuran and the like.

When a compound of formula I is obtained wherein R or $R_1$ or both R and $R_1$ are $-NR_4R_5$ and at least one of $R_4$ and $R_5$ represents hydroxy-($C_1$-$C_4$)alkyl, it can be tranformed into the corresponding halogen-($C_1$-$C_4$)alkyl derivatives by technics known per se in the art. These compounds, and preferably the chloro-($C_1$-$C_4$)alkyl derivatives, can in turn be reacted with an alkali metal cyanide (MeCN) or an alkali metal ($C_1$-$C_4$)alkoxide to give the corresponding compounds of formula I wherein $R_4$ and/or $R_5$ independently contain a ($C_1$-$C_4$)alkyl group substituted with a cyano group or an alkoxide group.

When the above compounds of formula I wherein $R_4$ and/or $R_5$ is a ($C_1$-$C_4$)alkylnitrile, the cyano function can be transformed according to a variety of known per se technics.

For instance, they can be transformed into the corresponding compounds wherein the cyano function is replaced by a ($C_1$-$C_4$)alkoxycarbonyl function.

This transformation is carried out by dissolving the cyano derivative in the appropriate hydroxy-($C_1$-$C_4$)alkyl solvent, passing a stream of gaseous hydrogen chloride through the mixture to saturation, heating the reaction system to the reflux, and recovering the product according to known per se technics.

The compounds I wherein R is a mercapto group which are obtained through cyclization of the hydrazinophthalazine of formula II with carbon disulfide, can also be further processed to give compounds I wherein R is ($C_1$-$C_4$)alkylthio, ($C_1$-$C_4$)alkylsulfinyl or ($C_1$-$C_4$)alkylsulfonyl. In particular, treatment of a compound I wherein R is mercapto with a ($C_1$-$C_4$)alkyl iodide, gives the corresponding compound wherein R is a ($C_1$-$C_4$)alkylthio group in good yields. This ($C_1$-$C_4$)alkylthio derivative can then be oxidized e.g. with m-chloro perbenzoic acid to give the corresponding ($C_1$-$C_4$)alkyl sulfinyl derivative or with hydrogen peroxide to give the corresponding ($C_1$-$C_4$)alkylsulfonyl derivative directly.

If desired, the ($C_1$-$C_4$)alkylsulfinyl derivative thus obtained can be transformed into the corresponding compounds I wherein R is an amino group

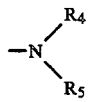

or an alkoxy or cycloalkoxy group $-OR_6$ wherein $R_4$, $R_5$, and $R_6$ are as defined before by reaction with an amine

or an alkoxide $MeOR_6$ according to the procedures outlined before.

An alternative method for preparing compounds of formula I wherein R is ($C_1$-$C_6$)alkyl, phenyl, substituted phenyl or carbo-($C_1$-$C_4$)alkoxy, consists in treating a 4-substituted-1-hydrazinophthalazine of formula II with an aldehyde of formula R'CHO, wherein R' stands for ($C_1$-$C_6$)alkyl, phenyl, substituted phenyl or carbo-($C_1$-$C_4$)-alkoxy followed by cyclization of the thus obtained hydrazone of formula III

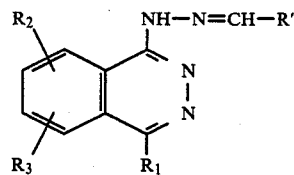

to the desired end product of formula I by treatment with an oxidizing agent. Among the several useful oxidizing agents which may be employed to carry out the oxidative cyclization are bromine, lead tetraacetate, N-bromoacetamide, manganese dioxide and the like. As for the first step which leads to the intermediate hydrazone III, it has been found that very high yields are obtained when an equimolar amount of the aldehyde R'CHO is added to a solution of an acid addition salt of the 1-hydrazino-phthalazine of formula II in water and the reaction mixture is heated with stirring for a few minutes.

The intermediate hydrazone of formula III is then precipitated from the aqueous acidic solution by alkalinization and is recovered by filtration. If desired, it can be purified, simply by crystallization from a suitable crystallization solvent, or it can be used as such in the following oxidative step. In the oxidative cyclization, which is carried out in the presence of an organic solvent that does not interfere with the reaction course, the oxidizing agent is employed in the same equivalent proportion as the hydrazone compound, or, preferably, in a slight excess.

When the reaction, which may be followed by thin layer chromatography, is complete, the reaction mixture can be conventionally worked up in order to remove or neutralize the excess of oxidizing agent and the obtained cyclization product is precipitated by diluting the reaction mixture with a large amount of cold water, separated by filtration and purified by crystallization.

According to a preferred embodiment this oxidative step is carried out by suspending the hydrazone of formula III in a lower alkanoic acid in the presence of the corresponding alkali metal salt, typically acetic acid in the presence of sodium acetate, and adding thereto a solution of bromine in the same lower alkanoic acid. The reaction smoothly proceeds at room temperature and is generally complete in a couple of hours. Recovery and purification of the thus obtained compound are carried out as illustrated above.

When, following the teachings set forth above, compounds of formula I are obtained wherein $R_1$ is a halogen atom, they can be transformed into the corresponding compounds of formula I wherein $R_1$ is a ($C_1$-$C_4$)alkylthio, amino or substituted amino and alkoxy or cycloalkoxy group by following the usual procedures illustrated above for the replacement of the 3-positioned chloro substituent.

It will be readily apparent to those skilled in the art that this last method is particularly convenient for preparing a series of triazolo-phthalazines having the same meanings for R, $R_2$, and $R_3$ but differing in the meanings of the substituents $R_1$ since in this case a common triazolo-phthalazine intermediate can be employed.

An alternative procedure for preparing the compounds of the invention wherein R is OR₆ as well as those compounds wherein R₁ is OR₉ consists in treating a 3-hydroxy-s-triazolo-phthalazine of the formula

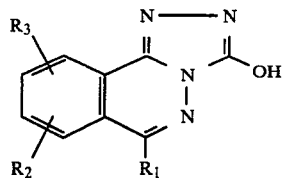

or a 6-hydroxy-s-triazolophthalazine of the formula

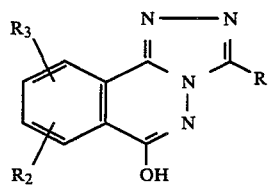

with an alkali metal hydride to give the corresponding alkali metal salt of the hydroxy function.

The alkali metal of the compound of formula V is then reacted with a compound of formula X—R, wherein R is as above and X is selected from chloro, bromo, and iodo, to give the desired product of formula I.

Similarly, the alkali metal salt of the compound of formula VI is reacted with a compound of formula X—R₁, wherein R₁ and X are as already defined, to give the desired product of formula I.

The compounds of formula V and VI can be prepared according to different methods. A convenient method for preparing them is by reacting, respectively, the corresponding 3-chloro or 6-chloro derivative, with anhydrous sodium acetate in glacial acetic acid. The starting 4-substituted-1-hydrazinophthalazines of formula II can be prepared by reaction of the appropriate 4-substituted-1-chloro-phthalazines of formula IV

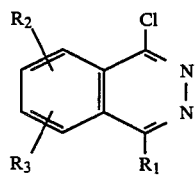

with hydrazine hydrate according to the procedures described by J. Druey and B. H. Ringier in Helv. Chim. Acta, 34, 195 (1951).

In their turn the 4-substituted-1-chloro-phthalazines of formula IV can be prepared by the conventional synthetic methods widely known in chemistry for the preparation of phthalazine derivatives.

An alternative way for preparing compounds of formula I wherein the 3-positioned substituent represents a (C₁-C₆alkyl, phenyl, substituted phenyl or carbo-(C₁-C₄)alkoxy group consists in treating directly the 4-substituted-1-chloro-phthalazine derivative of formula IV with an excess of a hydrazine derivative of formula

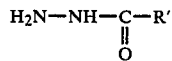

wherein R' has the same meanings as above. This reaction is preferably conducted in a suitable inert organic solvent, such as a lower alkanol, dioxane or tetrahydrofuran, at the reflux temperature. The desired cyclized product of formula I so obtained is then isolated and purified using standard isolation and purification techniques well known to those skilled in the art. Thus, for example, the reaction mixture is concentrated to dryness and the residue is carefully washed with water and crystallized from a suitable organic solvent.

The following examples describe in details some of the compounds of the invention and illustrate the process for preparing them without limiting the scope of the present invention.

EXAMPLE 1

6-Chloro-3-phenyl-1,2,4-triazolo[3,4-a]phthalazine

Concentrated HCl is gradually added to a suspension of 1-hydrazino-4-chloro-phthalazine (0.1 mole) in water (900 ml) until a clear solution is obtained. Then benzaldehyde (0.1 mole) dissolved in the smallest amount of ethanol possible, is dripped into the obtained solution which is heated to 60°/70° C. and stirred for 10 minutes. The reaction mixture is then cooled, and brought to pH 8 by the addition of aqueous sodium bicarbonate. The hydrazone which forms is recovered by filtration and crystallized from isopropanol (m.p. 174°–75° C.). This hydrazone (0.1 mole) is then suspended in acetic acid (900 ml) containing anhydrous sodium acetate (0.3 mole) and to the obtained suspension a solution of bromine (0.105 mole) in acetic acid (60 ml) is added dropwise. After vigorously stirring for 60 minutes, the reaction mixture is poured into ice-water (5 l) and the solid which separates is recovered by filtration, washed first with a diluted aqueous solution of sodium metabisulfite and then with water, and finally crystallized from isopropanol yielding the compound of the title in 74% yield. M.p. 172°–74° C. Using essentially the same procedure outlined in example 1 above, a number of other 3-substituted-6-chloro-1,2,4-triazolo[3,4-a]phthalazines are prepared having the general formula

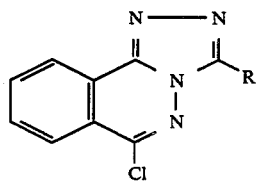

These compounds, as well as the hydrazone intermediates of formula

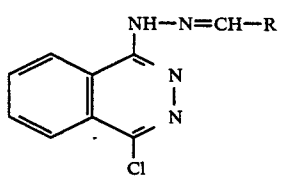

are described in Table I below.

TABLE I

| Ex. No. | R | M.p. (°C.) | Crystalliz. Solvent | % Yield | M.p. (°C.) and crystallization solvent of the intermediate IIIa, if isolated |
|---|---|---|---|---|---|
| 2 | 4-OCH₃-C₆H₄- | 193–94 | Isopropanol | 82 | 175–77 (Methyl Cellosolve ®) |
| 3 | 4-biphenylyl | 220–22 | Methyl Cellosolve ® | 85 | 192–94 (Isopropanol) |
| 4 | 2,4,5-tri-OCH₃-C₆H₂- | 189–91 | Methanol | 73 | 216–18 (Methyl Cellosolve ®) |
| 5 | 4-NHCOCH₃-C₆H₄- | 306–8 | Methyl Cellosolve ® | 85 | 222–24 (Methyl Cellosolve ®) |
| 6 | 3-Br-4-OC₂H₅-5-Br-C₆H₂- | 184–86 | Ethanol | 63 | 184–87 (Methyl Cellosolve ®) |
| 7 | 3-Br-4-OCH₃-5-OCH₃-C₆H₂- | 222–24 | Methyl Cellosolve ® | 82 | 206–08 (Ethanol) |
| 8 | 3,4,5-tri-OC₂H₅-C₆H₂- | 152–53 | Methanol | 70 | 170–72 (Methyl Cellosolve ®) |
| 9 | 4-N(CH₃)₂-C₆H₄- | 246–48 | Methyl Cellosolve ® | 49 | 173–75 (Ethanol) |
| 10 | 3-Cl-4-N(CH₃)₂-C₆H₃- | 281–83 | Methyl Cellosolve ® | 46 | 233–36 (Methyl Cellosolve ®) |
| 11 | 5-Cl-2-Br-4-N(CH₃)₂-C₆H₂- | 248–51 | Methyl Cellosolve ® | 40 | |

TABLE I-continued

| Ex. No. | R | M.p. (°C.) | Crystalliz. Solvent | % Yield | M.p. (°C.) and crystallization solvent of the intermediate IIIa, if isolated |
|---|---|---|---|---|---|
| 12 | –C₆H₄–CONH₂ | 308–09 | Dimethylformamide | 89 | 285–88 (Methyl Cellosolve ®) |
| 13 | 2-CH₃-C₆H₄– | 158–160 | Ethanol | 80 | 173–175 (Ethanol/Chloroform) |
| 14 | 4-CH₃-C₆H₄– | 201–203 | Ethanol/Chloroform | 81 | 177–178 (Ethanol/Chloroform) |

EXAMPLE 15

3-(2-bromophenyl)-6-chloro-1,2,4-triazolo[3,4-a]phthalazine

A solution of 2-bromobenzoyl chloride (0.12 mole) in dioxane (50 ml) is added to a mixture of 1-hydrazino-4-chlorophthalazine (0.1 mole), triethylamine (0.12 mole) and dioxane (200 ml). The reaction mixture is refluxed for five hours then the solvent is evaporated off and the obtained residue is washed with a small amount of water and crystallized from methanol giving the compound of the title in 60% yield. M.p. 203°–04° C.

By following essentially the same procedure described in the foregoing example, other triazolo[3,4-a]phthalazines of formula Ia are prepared.

These compounds are described in Table II below.

TABLE II

| Ex. No. | R | M.p. (°C.) | Crystallization solvent | % Yield |
|---|---|---|---|---|
| 16 | —CH₃ | 197–99 | Ethanol/Chloroform | 60 |
| 17 | 4-Cl-C₆H₄– | 166 | Ethanol | 74 |
| 18 | 2,?-(CH₃)₂-C₆H₄– | 203–04 | Isopropanol | 81 |
| 19 | 4-F-C₆H₄– | 174–76 | Methanol | 65 |
| 20 | 2-Cl-5-NO₂-C₆H₃– | 251–53 | Methyl Cellosolve ® | 75 |
| 21 | 2-OCH₃-5-O(CH₂)₄CH₃-C₆H₃– | 150–51 | Ethanol | 82 |
| 22 | 4-CN-C₆H₄– | 251–53 | Methyl Cellosolve ® | 76 |
| 23 | 3,4-(OCH₃)₂-C₆H₃– | 235–37 | Methyl Cellosolve ® | 62 |
| 24 | 3-CF₃-C₆H₄– | 194–96 | Ethanol/Chloroform | 62 |
| 25 | 4-OCOCH₃-C₆H₄– | 233–36 | Ethanol/Chloroform | 78 |
| 26 | 2-Cl-C₆H₄– | 199–201 | Ethanol/Chloroform | 71 |

EXAMPLE 27

3-phenyl-6-(1-pyrrolidinyl)-1,2,4-triazolo[3,4-a]phthalazine

A mixture of 6-chloro-3-phenyl-1,2,4-triazolo[3,4-a]phthalazine (5 g), pyrrolidine (5 ml), ethanol (35 ml) and catalytic amounts of KI, is poured in a pressure resistant vessell and heated to 100° C. for 8 hours. The reaction mixture is then cooled, the solvent is evaporated off and the residue is thoroughly washed with a small amount of water and crystallized from ethanol yielding the compound of the title in 82% yield. M.p. 208°–09° C.

EXAMPLE 28 to 84

The compounds of examples 28 to 84, listed in Table III below, are prepared by following essentially the same procedure outlined in example 27 above.

TABLE III

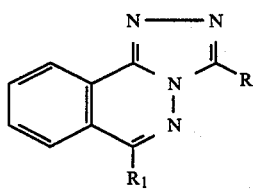

| Ex. No. | R | R₁ | M.p. (°C.) | Crystallization solvent | % Yield |
|---|---|---|---|---|---|
| 28 | phenyl | —N(CH₂CH₂OCH₃)₂ | 111-12 | Ethyl ether | 60 |
| 29 | phenyl | —N(CH₃)—CH₂—CH(OH)—CH₃ | 165-68 | Methanol | 55 |
| 30 | phenyl | morpholino | 198 | Ethanol | 62 |
| 31 | 4-OCH₃-phenyl | —N(CH₃)—CH₂—CH(OH)—CH₃ | 167-68 | Methanol | 57 |
| 32 | 4-OCH₃-phenyl | —N(CH₃)—CH₂—CH₂—CH₂—OH | 173-175 | Ethanol | 78 |
| 33 | phenyl | 4-phenylpiperazin-1-yl | 154-55 | Methyl Cellosolve ® | 50 |
| 34 | phenyl | —NH₂ | 314-16 | Methyl Cellosolve ® | 54 |
| 35 | phenyl | —NHCH₃ | 318-19 | Methyl Cellosolve ® | 76 |
| 36 | phenyl | —NHC₂H₅ | 289-90 | Methyl Cellosolve ® | 74 |
| 37 | phenyl | —NHCH(CH₃)₂ | 269-70 | Methyl Cellosolve ® | 54 |
| 38 | phenyl | —NHCH₂-phenyl | 283-84 | Methyl Cellosolve ® | 92 |

TABLE III-continued

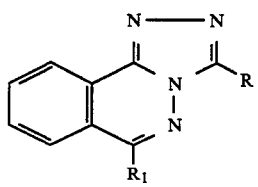

| Ex. No. | R | $R_1$ | M.p. (°C.) | Crystallization solvent | % Yield |
|---|---|---|---|---|---|
| 39 | phenyl | $-NH-(CH_2)_3-CH_3$ | 254–55 | Methyl Cellosolve ® | 75 |
| 40 | phenyl | $-NHC(CH_3)_3$ | 241–44 | Ethanol | 72 |
| 41 | phenyl | $-N(CH_3)_2$ | 177–78 | Ethanol | 85 |
| 42 | phenyl | $-N(C_2H_5)_2$ | 115–16 | Ethanol | 63 |
| 43 | phenyl | piperidinyl | 198–200 | Ethanol | 67 |
| 44 | phenyl | 4-methylpiperazinyl | 171–72 | Ethanol | 80 |
| 45 | phenyl | 3,3-dimethylazetidinyl | 227–29 | Ethanol | 70 |
| 46 | phenyl | $-N(CH_3)(C_2H_5)$ | 114–16 | Methanol | 56 |
| 47 | 4-methoxyphenyl | pyrrolidinyl | 228–29 | Methyl Cellosolve ® | 93 |
| 48 | 2-bromophenyl | pyrrolidinyl | 204–06 | Ethanol/Chloroform | 86 |
| 49 | biphenyl | pyrrolidinyl | 253–54 | Ethanol/Chloroform | 80 |

TABLE III-continued

[Structure: phthalazine fused with triazole, with substituent R on triazole carbon and R₁ at position shown]

| Ex. No. | R | R₁ | M.p. (°C.) | Crystallization solvent | % Yield |
|---|---|---|---|---|---|
| 50 | 4-CN-C₆H₄- | —N(pyrrolidine) | 276–78 | Ethanol/Chloroform | 58 |
| 51 | 4-NHCOCH₃-C₆H₄- | —N(pyrrolidine) | 333–35 | Chloroform | 87 |
| 52 | 4-N(CH₃)₂-C₆H₄- | —N(pyrrolidine) | 233–35 | Ethanol | 89 |
| 53 | 3,4-(CH₃)₂-C₆H₃- | —N(pyrrolidine) | 184–86 | Ethanol | 90 |
| 54 | 3,4-(OCH₃)₂-C₆H₃- | —N(pyrrolidine) | 229–31 | Ethanol | 87 |
| 55 | 3-OCH₃-4-O(CH₂)₄CH₃-C₆H₃- | —N(pyrrolidine) | 176–78 | Ethanol | 94 |
| 56 | 3-Cl-4-N(CH₃)₂-C₆H₃- | —N(pyrrolidine) | 216–19 | Ethanol | 80 |
| 57 | 3-NO₂-4-Cl-C₆H₃- | —N(pyrrolidine) | 278–80 | Ethanol/Chloroform | 56 |
| 58 | 3-NO₂-4-(pyrrolidin-1-yl)-C₆H₃- | —N(pyrrolidine) | 248–50 | Ethanol/Chloroform | 16 |

TABLE III-continued
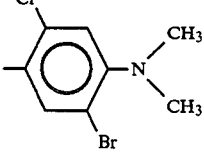
| Ex. No. | R | $R_1$ | M.p. (°C.) | Crystallization solvent | % Yield |
|---|---|---|---|---|---|
| 59 |  | 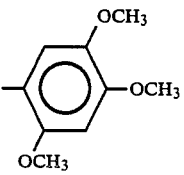 | 226–27 | Ethanol | 78 |
| 60 |  | 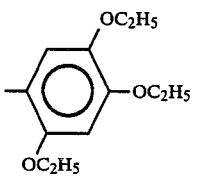 | 217–18 | Ethanol | 78 |
| 61 |  | 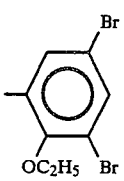 | 220–22 | Ethanol | 77 |
| 62 |  | 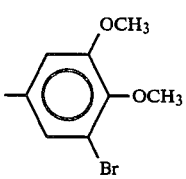 | 194–96 | Ethanol/Chloroform | 88 |
| 63 |  | 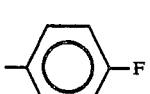 | 229–31 | Ethanol/Chloroform | 57 |
| 64 |  | 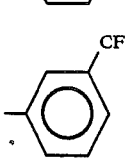 | 222–25 | Ethanol/Chloroform | 90 |
| 65 |  |  | 217–19 | Ethanol/Chloroform | 87 |
| 66 | —CH$_3$ | 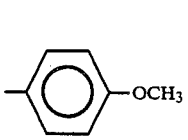 | 208–09 | Methanol | 84 |
| 67 |  | —N(CH$_2$CH$_2$OCH$_3$)$_2$ | 100–01 | Ethyl ether/Petroleum ether | 75 |

TABLE III-continued

| Ex. No. | R | $R_1$ | M.p. (°C.) | *Crystallization solvent | % Yield |
|---|---|---|---|---|---|
| 68 | —C₆H₄—OCH₃ | —NHCH₂CH₂—C₆H₅ | 275–77 | Ethanol/Chloroform | 88 |
| 69 | —C₆H₄—OCH₃ | —N(CH₃)CH₂CH₂—C₆H₅ | 146–48 | Methanol | 50 |
| 70 | —C₆H₄—OCH₃ | —NHCH₂CH₂—C₆H₃(OCH₃)₂ | 257–59 | Ethanol/Chloroform | 88 |
| 71 | —C₆H₄—OCH₃ | —N(CH₃)CH₂CH₂—C₆H₃(OCH₃)₂ | 158–59 | Methanol | 67 |
| 72 | —C₆H₄—OCH₃ | —N(piperidinyl)-COOC₂H₅ | 225–27 | Ethanol/Chloroform | 88 |
| 73 | —C₆H₅ | —N(3,5-dimethylpiperidinyl) | 197–99 | Methanol | 85 |
| 74 | —C₆H₄—OH | —N(pyrrolidinyl) | 345–48 | Dimethylformamide | 91 |
| 75 | —C₆H₄—NH₂ | —N(pyrrolidinyl) | 308–10 | Ethanol/Chloroform | 75 |
| 76 | —C₆H₄—CONH₂ | —N(pyrrolidinyl) | 305–07 | Ethanol/Chloroform | 84 |
| 77 | —C₆H₄—COOH | —N(pyrrolidinyl) | >340 | Methyl Cellosolve ® | 37 |

TABLE III-continued

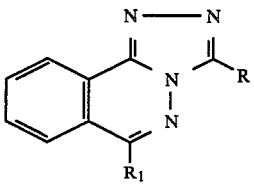

| Ex. No. | R | R₁ | M.p. (°C.) | Crystallization solvent | % Yield |
|---|---|---|---|---|---|
| 78 | 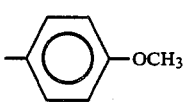 | 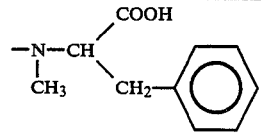 | 205–08 | Methanol | 45 |
| 79 | 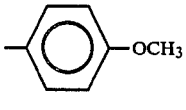 | 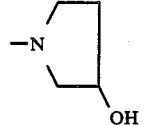 | 271–73 | Ethanol/Chloroform | 88 |
| 80 | 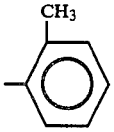 | —N(CH₂CH₂OCH₃)₂ | | Ethyl Acetate | 71 |
| 81 | 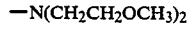 | —N(CH₂CH₂OCH₃)₂ | 133–135 | Ethyl Acetate | 77 |
| 82 | 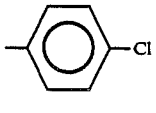 | —N(CH₂CH₂OCH₃)₂ | 126–127 | Ethyl Acetate | 78 |
| 83 | 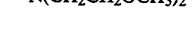 | —N(CH₂CH₂OCH₃)₂ | 104–105 | Ethyl Acetate | 78 |
| 84 | 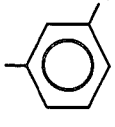 | —N(CH₂CH₂OCH₃)₂ | 122–124 | Ethyl Acetate | 80 |

EXAMPLE 85

6-ethoxy-3-phenyl-1,2,4-triazolo[3,4-a]phthalazine

6-Chloro-3-phenyl-triazolo[3,4-a]phthalazine (9.9 g) is added to a solution of sodium ethoxide (2.7 g) in absolute ethanol (45 ml). The reaction mixture is heated to 100° C. in a pressure-resistant vessel. After 8 hours, the reaction mixture is cooled and concentrated to dryness. The obtained residue is washed carefully with a small amount of water and then is crystallized from isopropanol yielding 7 g of the compound of the title. M.p. 172°–73° C.

EXAMPLE 86

3-(2-bromophenyl)-6-ethoxy-1,2,4-triazolo [3,4-a]phthalazine 3-(2-Bromophenyl)-6-chloro-triazolo-1,2,4-triazolo[3,4-a]phthalazine (0.01 mole) is added to a mixture of sodium ethoxide (0.012 mole) in dimethylformamide (50 ml). The reaction mixture is stirred at 50° C. for 2 hours and is then concentrated to dryness under vacuum. The residue is washed with a small amount of water and crystallized from methanol giving the compound of the title in 68% yield. M.p. 157°–58° C.

EXAMPLES 87 TO 101

The 6-ethoxy-3- substituted-triazolo[3,4-a]phthalazinens of the formula

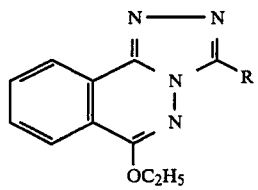

Ib which are described in Table IV below, are prepared by following essentially the procedure described in example 86 above.

| Ex. No. | R | M.p. (°C.) | Crystal-lization solvent | % Yield |
|---|---|---|---|---|
| 87 | biphenyl | 223–24 | Ethanol | 65 |
| 88 | 4-N(CH3)2-phenyl | 207–10 | Methanol | 73 |
| 89 | 4-CN-phenyl | 232–34 | Methanol | 50 |
| 90 | 4-NHCOCH3-phenyl | 306–09 | Methyl Cellosolve ® | 83 |
| 91 | 2,3-(CH3)2-phenyl | 190–91 | Methanol | 80 |
| 92 | 2-NO2, 3-Cl-phenyl | 213–15 | Methyl Cellosolve ® | 42 |
| 93 | 3-OCH3, 4-O(CH2)4CH3-phenyl | 153–54 | Methanol | 87 |
| 94 | 3,4-(OCH3)2-phenyl | 204–05 | Methanol | 87 |
| 95 | 3-Cl, 4-N(CH3)2-phenyl | 229–30 | Methanol | 64 |
| 96 | 3,4,5-(OCH3)3-phenyl | 228–30 | Ethanol | 96 |
| 97 | 3,4,5-(OC2H5)3-phenyl | 178–80 | Methanol | 77 |
| 98 | 3,5-Br2, 4-OC2H5-phenyl | 155–57 | Methanol | 78 |
| 99 | 3,4-(OCH3)2, 5-Br-phenyl | 212–13 | Methanol | 78 |
| 100 | 3-Cl, 4-N(CH3)2, 5-Br-phenyl | 192–94 | Methanol | 70 |
| 101 | 4-OCH3-phenyl | 192–94 | Ethanol | 74 |

Essentially following the procedure of example 86 the following compounds of examples 102 to 104 are prepared:

EXAMPLE 102

6-(2-hydroxyethoxy)-3-(4-methoxyphenyl)-1,2,4-triazolo[3,4-a]phthalazine

Crystallization solvent: ethanol/chloroform. Yield 89%. M.p. 252°–254° C.

EXAMPLE 103

6-(4-hydroxybutoxy)-3-(4-methoxyphenyl)-1,2,4-triazolo[3,4-a]phthalazine

Crystallization solvent: ethanol/chloroform. Yield: 40%. M.p. 180°–182° C.

EXAMPLE 104

4[[3-(4-methoxyphenyl)-1,2,4-triazolo[3,4-a]phthalazin-6-yl]oxy]butanoic acid ethyl ester.

Crystallization solvent: ethyl acetate/ethyl ether. Yield 59%. M.p. 114°–117° C.

EXAMPLE 105

6-(2-methoxyethoxy)-3-(4-methoxyphenyl)-1,2,4-triazolo[3,4-a]phthalazine

6-Chloro-3-(4-methoxyphenyl)-1,2,4-triazolo-3,4-a]phthalazine (4.5 g) is added to a solution of sodium (0.4 g) in 2-methoxyethanol (80 ml) and the obtained reaction mixture is refluxed for 6 hours. The solvent is then evaporated off and the residue is washed with water and crystallized from methanol yielding 2.9 g of the compound of the title. M.p. 174°–76° C.

EXAMPLE 106

N-(3-chloropropyl)-N-methyl-3-(4-methoxyphenyl)-1,2,4-triazolo[3,4-a]phthalazin-6-amine To 2.8 g of N-(3-hydroxypropyl)-N-methyl-3-(4-methoxy phenyl)-1,2,4-triazolo[3,4-a]phthalazin-6-amine (the compound of example 32) dissolved in chloroform (30 ml) are added a few drops of N,N-dimethylformamide and then 1.1 ml of thionyl chloride in chloroform (5 ml). The mixture is refluxed for about 5 hours. After cooling to room temperature, the mixture is concentrated to dryness and the residue is taken up with cold aqueous sodium bicarbonate. The product of the title is collected after filtration and crystallized from ethanol. Yield 85%. M.p. 113°–115° C.

EXAMPLE 107

4-[[3-(4-methoxyphenyl)-1,2,4-triazolo[3,4-a]phthalazin-6-yl]methylamino]butanonitrile The compound of example 106 (2.5 g) is dissolved in ethanol (20 ml) and added of potassium iodide (0.4 g) and potassium cyanide (0.75 g). The mixture is refluxed for about 8 hours. The reaction mixture is then hot filtered, and the filtrate is concentrated to dryness. The residue is taken up with water and extracted with methylene chloride (2×25 ml). The pooled organic layer is dried over sodium sulfate and concentrated to dryness. The residue, which is the compound of the title, crystallizes from methanol. Yield: 70%. M.p. 117°–119° C.

EXAMPLE 108

4-[[3-(4-methoxyphenyl)-1,2,4-triazolo[3,4-a]phthalazin-6-yl]methylamino]butanoic acid ethyl ester The compound of the foregoing example (3.8 g) is dissolved in ethanol (50 ml). The cold alcoholic solution is saturated with dry hydrogen chloride. The mixture is refluxed for about 6 hours, cooled to room temperature and then the solvent is stripped under reduced pressure. The residue is taken up with cold aqueous sodium bicarbonate and filtered. The collected solid is crystallized by ethyl ether to give the compound of the title. Yield: 57%. M.p. 103°–105° C.

EXAMPLE 109

6-ethylthio-3-phenyl-1,2,4-triazolo[3,4-a]phthalazine

50% Sodium hydride in mineral oil (1 g) is suspended in anhydrous dimethylformamide (50 ml) and stirred for 10 minutes. Then a solution of ethanethiol (1.5 ml) in anhydrous dimethylformamide (10 ml) is slowly added thereto and the resulting mixture is stirred at room temperature for 30 minutes. Finally 6-chloro-3-phenyl-1,2,4-triazolo[3,4-a]phthalazine (5.9 g) is added and the reaction mixture is heated at 50° C. for five hours. The solvent is evaporated off under *vacuum* and the obtained residue is washed a few times with water and then is crystallized from isopropanol yielding 4.7 g of the compound of the title. M.p. 190°–91° C.

EXAMPLE 110

3-phenyl-1,2,4-triazolo[3,4-a]-phthalazin-6-thiolo

The reaction is carried out essentially as in the above example but using an excess of ethanethiol (7 ml). M.p. 203°–204° C. (isopropanol).

EXAMPLE 111

6-ethylsulfinyl-3-phenyl-1,2,4-triazolo[3,4-a]phthalazine m-Chloroperbenzoic acid (3.1 g) is added to a solution of the compound of example 109 (4.6 g) in methylene chloride (50 ml) and the reaction mixture is stirred at room temperature for five hours. The mixture is washed first with diluted sodium metabisulfite and then with aqueous sodium bicarbonate.

The organic solution is dried over $Na_2SO_4$ and then the solvent is evaporated off giving a raw residue which is purified by crystallization from ethanol yielding 3.7 g of the compound of the title. M.p. 147°–49° C.

EXAMPLE 112

6-(ethyl-sulfonyl)-3-phenyl-1,2,4-triazolo[3,4-a]phthalazine

To a suspension of the compound of example 109 (4.6 g) in glacial acetic acid (65 ml), 36% $H_2O_2$ (5.7 ml) is added and the reaction mixture is allowed to stand at room temperature for 94 hours. The mixture is then diluted with cold water (200 ml) and the solid is recovered by filtration and crystallized from isopropanol yielding 4.3 g of the compound of the title. M.p. 187°–189° C.

EXAMPLE 113

6-phenyl-1,2,4-triazolo[3,4-a]phthalazin-3-thiolo and 6-phenyl-N-(2-propenyl)-1,2,4-triazolo[3,4-a]phthalazin-3-amine 2-Propenyl-isothiocyanate (16.9 g) is added dropwise to a suspension of 1-hydrazino-4-phenylphthalazine (40 g) in anhydrous methanol (200 ml).

The mixture is stirred at room temperature for about 1 hour and then filtered. 49 Grams of the collected solid (m.p. 150°–170° C.) are suspended in glacial acetic acid (750 ml) and refluxed for about 6 hours. The cooled mixture is filtered recovering 14.8 g of 6-phenyl-1,2,4-triazolo[3,4-a]phthalazin-3-thiolo. M.p. 301°–303° C. (ethanol/chloroform). The filtered acetic acid solution is then evaporated to dryness. The residue is washed with water, dried, dissolved in methylene chloride, and thoroughly washed with aqueous sodium bicarbonate. The solvent is then evaporated under reduced pressure and the residue is crystallized from ethyl acetate yielding 16.2 g of 6-phenyl-N-(2-propenyl)-1,2,4-triazolo-[3,4-a]phthalazin-3-amine. M.p. 175°–176° C.

EXAMPLE 114

6-phenyl-1,2,4-triazolo[3,4-a]phthalazine

A mixture of 4-phenyl-1-hydrazinophthalazine (30 g) and triethylorthoformate (200 ml) is refluxed for 3 hours, then the excess of the orthoformate is evaporated off and the residue is crystallized from ethanol yielding 26 g of the compound of the title. M.p. 198°–99° C.

EXAMPLE 115

8-chloro-6-phenyl-1,2,4-triazolo[3,4-a]phthalazine

The compound of the title is prepared by following essentially the same procedure outlined in example 114 above but using 6-chloro-4-phenyl-1-hydrazinophthalazine instead of 4-phenyl-1-hydrazinophthalazine. M.p. 189°–90° C. (from ethanol).

EXAMPLE 116

8-chloro-3-methyl-6-phenyl-1,2,4-triazolo[3,4-a]phthalazine

A mixture of 1,6-dichloro-4-phenyl-phthalazine (8 g), acetyl hydrazine (4.4 g) and butanol (100 ml) is refluxed for 25 hours. Then the solvent is evaporated off and the residue is washed carefully with a small amount of water and crystallized from ethanol yielding 6 g of the compound of the title. M.p. 236°–38° C.

EXAMPLE 117

6-phenyl-1,2,4-triazolo[3,4-a]phthalazine-3-thiolo

Aqueous 15% KOH (50 ml) and carbon disulfide (16.4 ml) are added to a suspension of 4-phenyl-1-hydrazinophthalazine (32.2 g) in ethanol (400 ml) and the obtained mixture is refluxed for 5 hours, and then concentrated to dryness. The residue is dissolved in hot 1% NaOH (1000 ml), the solution is filtered and acidified by the addition of acetic acid. The compound of the title is recovered by filtration and purified by crystallization from ethanol/chloroform yielding 35.8 g of pure compound. M.p. 301°–03° C.

EXAMPLES 118 and 119

The compounds of the following examples are prepared by following substantially the same procedure outlined in example 117 above but starting from the proper 1-hydrazinophthalazine derivative indicated between parenthesis:

EXAMPLE 118

6-(4-methoxyphenyl)-1,2,4-triazolo[3,4-a]phthalazin-3-thiolo (from 4-(4-methoxyphenyl)-1-hydrazinophthalazine)

Yield: 93%. M.p. 314°–17° C. (from ethanol/chloroform).

EXAMPLE 119

8-chloro-6-phenyl-1,2,4-triazolo[3,4-a]phthalazin-3-thiolo (from 6-chloro-4-phenyl-1-hydrazinophthalazine)

Yield: 88%. M.p. 328°–30° C. (from ethanol/chloroform).

EXAMPLE 120

3-chloro-6-phenyl-1,2,4-triazolo[3,4-a]phthalazine

A moderate chlorine stream is bubbled through a mixture of 6-phenyl-1,2,4-triazolo[3,4-a]phthalazine-3-thiolo (12 g), chloroform (200 ml) and water cooled to 0/+5° C., over a period of 3 hours. Then the temperature is allowed to increase to 20° C. and the organic phase is separated, dried over MgSO$_4$ and concentrated to dryness. The obtained residue is crystallized from Methyl Cellosolve ® yielding 7.8 g of the compound of the title which melts at 229°–30° C.

EXAMPLE 121

3,8-dichloro-6-phenyl-1,2,4-triazolo[3,4-a]phthalazine

The compound of the title is prepared by following substantially the procedures described in example 120 above but starting from 8-chloro-6-phenyl-1,2,4-triazolo[3,4-a]phthalazin-3-thiolo. Yield 55%. M.p. 230°–33° C. (from Methyl Cellosolve ®).

EXAMPLE 122

6-phenyl-3-(1-pyrrolidinyl)-1,2,4-triazolo[3,4-a]phthalazine

A mixture of 3-chloro-6-phenyl-1,2,4-triazolo[3,4-a]phthalazine (4.5 g), pyrrolidine (6 ml) and ethanol (40 ml) is poured in a steel cylinder and heated to 100° C. for 8 hours. Then the mixture is cooled, and concentrated to dryness by evaporating off the solvent. The obtained residue is washed with water and crystallized from ethanol giving 3.5 g of the compound of the title. M.p. 245°–47° C.

EXAMPLE 123

8-chloro-6-phenyl-3-(1-pyrrolydinyl)-1,2,4-triazolo[3,4-a]phthalazine

The compound of the title is prepared by following the method described in the foregoing example but using 3,8-dichloro-6-phenyl-1,2,4-triazolo[3,4-a]phthalazine instead of 3-chloro-6-phenyl-1,2,4-triazolo[3,4-a]phthalazine. Yield: 82%. M.p. 245°–48° C. (from ethanol chloroform).

EXAMPLE 124

8-chloro-6-phenyl-3-[(2-hydroxypropyl)methylamino]-1,2,4-triazolo[3,4-a]phthalazine The compound of the title is prepared by following substantially the same procedure outlined in example 122 but starting from 3,8-dichloro-6-phenyl-1,2,4-triazolo[3,4-a]phthalazine and (2-hydroxypropyl)methylamine. Yield: 73%. M.p. 236°–38° C. (from ethanol/chloroform).

EXAMPLE 125

8-chloro-3-ethoxy-6-phenyl-1,2,4-triazolo[3,4-a]phthalazine

A mixture of 3,8-dichloro-6-phenyl-1,2,4-triazolo[3,4-a]phthalazine (5 g), sodium ethoxide (1.3 g) and absolute ethanol (40 ml) is poured into a steel bomb and heated to 100° C. for 8 hours. Then the mixture is cooled and concentrated to dryness. The obtained residue is triturated with water, filtered and crystallized from ethanol/chloroform yielding 3.3 g of the compound of the title. M.p. 226°–28° C.

EXAMPLE 126

8-chloro-3-isopropyl-6-phenyl-1,2,4-triazolo[3,4-a]phthalazine

Isobutyrroyl chloride (2.8 g) is added to a mixture of 6-chloro-1-hydrazino-4-phenyl-phthalazine (6.5 g), triethylamine (2.5 g) and anhydrous dioxane (70 ml). The obtained reaction mixture is refluxed for 5 hours, then the solvent is evaporated off and the residue is washed carefully with a small amount of water and finally is crystallized from ethanol/chloroform yielding 6.1 g of the compound of the title. M.p. 214°–16° C.

EXAMPLES 127 and 128

The following compounds are prepared by following exactly the same procedure outlined in example 126 above but using instead of isobutyrroyl chloride, the acid derivative starting material indicated between parenthesis.

EXAMPLE 127

8-chloro-3-(3-chlorophenyl)-6-phenyl-1,2,4-triazolo[3,4-a]phthalazine (from 3-chlorobenzoyl chloride)

Yield: 82%. M.p. 227°–30° C. (from ethanol/chloroform).

EXAMPLE 128

3-carbethoxy-8-chloro-6-phenyl-1,2,4-triazolo[3,4-a]phthalazine (from oxalic acid monoethyl ester monochloride)

Yield: 77%. M.p. 266°–68° C. (from ethanol/chloroform).

EXAMPLE 129

6-(4-methoxyphenyl)-3-(methylthio)-1,2,4-triazolo[3,4-a]phthalazine 6-(4-Methoxyphenyl)-1,2,4-triazolo[3,4-a]phthalazin-3-thiolo (4.2 g) is added to a solution of KOH (0.9 g) in methanol (32 ml) and the whole is stirred at room temperature for 10 minutes. Then methyl iodide (2.1 g) is slowly dripped into the mixture which is further stirred at room temperature for 4 hours. The reaction mixture is diluted with water (100 ml), the solid is recovered by filtration and crystallized from ethanol/chloroform yielding 4.1 g of the compound of the title. M.p. 218°–20° C.

EXAMPLE 130

3-methylthio-6-phenyl-1,2,4-triazolo[3,4-a]phthalazine

It is obtained essentially by following the procedure of the foregoing example, but substituting 6-phenyl-1,2,4- triazolo[3,4-a]phthalazine for 6-(4-methoxyphenyl)-1,2,4-triazolo[3,4-a]phthalazin-3-thiolo. M.p. 220°–221° C. (chloroform/methanol).

EXAMPLE 131

6-(4-methoxyphenyl)-3-(methylsulfinyl)-1,2,4-triazolo[3,4-a]phthalazine

3-Chloroperbenzoic acid (2.2 g) is added to a solution of 6-(4-methoxyphenyl)-3-(methylthio)-1,2,4-triazolo[3,4-a]phthalazine (4 g) in methylene chloride (120 ml) and the obtained mixture is stirred at room temperature for 5 hours. The solution is washed with sodium metabisulfite first and then with sodium bicarbonate. The organic solution is then dried over MgSO$_4$ and concentrated to dryness by evaporating off the solvent. The residue thus obtained is crystallized from ethanol yielding 4 g of the compound of the title. M.p. 201°–03° C.

EXAMPLE 132

3-methylsulfinyl-6-phenyl-1,2,4-triazolo[3,4-a]phthalazine

This compound is obtained by following the procedure of the foregoing example but substituting 6-phenyl-3-methylthio-1,2,4-triazolo[3,4-a]phthalazine for 6-(4-methoxyphenyl)-3-methylthio-1,2,4-triazolo[3,4-a]phthalazine. M.p. 215°–217° C. (Methylcellosolve ®).

EXAMPLE 133

6-(4-methoxyphenyl)-3-(1-pyrrolidinyl)-1,2,4-triazolo[3,4-a]phthalazine

A mixture of 6-(4-methoxyphenyl)-3-(methylsulfinyl)-1,2,4-triazolo[3,4-a]phthalazine (3.5 g) and pyrrolidine (30 ml) is heated to 120°/140° C. in a steel bomb for 16 hours. The mixture is then cooled, and the excess of the amine is evaporated off yielding a residue which is washed carefully with a small amount of water and crystallized from 70% ethanol. Yield: 45%. M.p. 196°–98° C.

EXAMPLE 134

Alternative preparation of 4-[[3-(4-methoxyphenyl)-1,2,4-triazolo[3,4-a]phthalazin-6-yl]-oxy-]butanoic acid ethyl ester.

6-hydroxy-3-(4-methoxyphenyl)-1,2,4-triazolo[3,4-a]phthalazine (2.9 g) is suspended in anhydrous N,N-dimethylformamide and added portionwise of 50% sodium hydride (0.5 g) in mineral oil. Under vigorous stirring, 4-chlorobutanoic acid ethyl ester (2 g) is added and the stirred mixture is gradually heated to 60°–70° C. and then kept to this temperature for about 14 h. The cooled mixture is then poured into water (400 ml). The separated water insoluble solid mass is then dissolved in methylene chloride, the solvent is then evaporated under reduced pressure and the obtained solid is crystallized from ethyl acetate/ethyl ether, giving the product of the title. (Yield 59%). M.p. 114°–117° C.

EXAMPLE 135

4-[methy[2-[[/3-(4-methoxyphenyl)-1,2,4-triazolo [3,4-a]phthalazin-6-yl]oxy]ethyl]amino]butanoic acid ethyl ester, citrate 4-[N-methyl-N-(2-hydroxyethyl)amino]butanoic acid ethyl ester (3.2 g), are dissolved in N,N-dimethylformamide (40 ml) and added portionwise of a suspension of 50% sodium hydride in mineral oil (0.8 g). The mixture is stirred for about 30 minutes and then added of 6-chloro-3-(4-methoxyphenyl)-1,2,4-triazolo[3,4-a]phthalazine. After heating to 60°–70° C. for about 5 hours, the solvent is evaporated under reduced pressure and the residue, which is the base corresponding to the product of the title, is taken up with water, extracted with chloroform, further purified by column chromatography and then isolated as the citrate salt by adding a slight excess of citric acid (15%). M.p. 142°–145° C. (methanol).

EXAMPLE 136

3-[[3-(4-methoxyphenyl)-1,2,4-triazolo[3,4-a]phthalazin-6-yl]oxy]-2-pyrrolidinone 6-Hydroxy-3-(4-methoxyphenyl)-1,2,4-triazolo[3,4-a]phthalazine, (9.8 g), is suspended in N,N-dimethylformamide (100 ml) and added of 50% sodium hydride in mineral oil (1.7 g). The mixture is heated to 50°–60° C.

and stirred for about 2 hours. After cooling to room temperature the mixture is added portionwise with 3-bromo-2-pyrrolidone (5.5 g). [This product is prepared according to F. Korte, H. Wanholf, Ber. 97, 1976 (1964)]. Then stirring is continued for about 5 hours at a temperature of about 70° C. The mixture is then cooled to room temperature and poured into water (800 ml). The residue, which is collected by filtration, is then crystallized from ethanol/chloroform. (Yield=82%). M.p. 290°-293° C.

EXAMPLE 137

4-amino-2-[[3-(4-methoxyphenyl)-1,2,4-triazolo[3,4-a]phthalazin-6-yl]oxy]butanoic acid, hydrochloride The compound of the foregoing example (8 g) is boiled in concentrated hydrochloric acid for about 8 hours. After evaporation to dryness and crystallization from ethanol/ethyl ether, the product of the title is obtained (yield=78%). M.p. 205°-208° C.

EXAMPLE 138

4-amino-2-[[3-(4-methoxyphenyl)-1,2,4-triazolo[3,4-a]phthalazin-6-yl]oxy]butanoic acid ethyl ester, hydrochloride The compound of the foregoing example is added to cold hydrogen chloride saturated alcoholic solution (250 ml). The mixture is refluxed for about 8 hours. The volatiles are removed by evaporation under reduced pressure and the residue is crystallized from ethanol-/ethyl ether. (Yield=81%). M.p. 208°-210° C.

Essentially following the procedure of the foregoing examples the following compounds of the general formula:

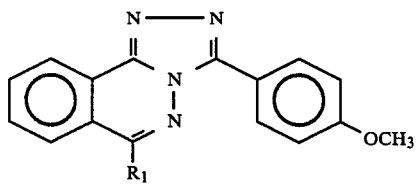

wherein $R_1$ is:

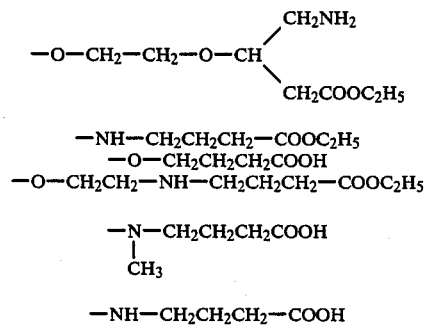

are obtained.

Preparation of the starting materials
The compounds
4-chloro-1-hydrazino-phthalazine ·
1-hydrazino-4-phenyl-phthalazine and
1-hydrazino-4-(4-methoxyphenyl)-phthalazine
employed as starting materials for preparing the compounds of examples 1 to 25, 113, 114, 117 and 118 are known from Helv. Chim. Acta 34, 195 (1951) and have been prepared by the method there described.

The compound 6-chloro-4-phenyl-1-hydrazino-phthalazine employed as starting material in examples 119, 126, 127 and 128 has been prepared with the following method: 2-benzoyl-4-chlorobenzoic acid (272 g) is dissolved in hot etanol (800 ml) and hydrazine hydrate (69 ml) is added to the obtained solution. The reaction mixture is refluxed for 1 hour and then cooled to low temperature. The crystalline solid which precipitates (204 g) is recovered by filtration. (M.p. 267°-69° C.). A mixture of the above product (200 g) and $POCl_3$ (600 ml) is heated to 100° C. for 1 hour and then cautiously poured in ice-water (5 l). During the addition, concentrated $NH_4OH$ is gradually drypped into the water so as to held the pH of the solution between 7 and 8. When the addition is terminated, the reaction mixture is stirred for 10 minutes and then filtered. The solid thus recovered is washed with water and crystallized from ethanol yielding 206 g of 1,6-dichloro-4-phenylphthalazine intermediate. (M.p. 189°-91° C).

This compound (210 g) is rapidly added to a mixture of ethanol (800 ml) and hydrazine hydrate (400 ml) heated to 50°-60° C. The reaction mixture is refluxed for 2 hours. Upon cooling, the compound of the title crystallizes out yielding 190 g. M.p. 185°-87° C.
Preparation of 6-hydroxy-3-(4-methoxyphenyl)-1,2,4-triazolo[3,4-a]phthalazine.

6-Chloro-3-(4-methoxyphenyl)-1,2,4-triazolo[3,4-a]phthalazine (0.5 mole) and fused anhydrous sodium acetate in acetic acid are heated to the reflux temperature for about 1 hour. The solvent is evaporated under reduced pressure, the residue is then taken up with water, collected by filtration, and crystallized from ethanol/chloroform. The product of the title is thus obtained in a 85% yield. M.p. 307°-309° C.

The pharmacological properties of the compounds of the present invention were first investigated by submitting them to the benzodiazepine receptor binding test in vitro. In this test, which was carried out by following essentially the method described by H. Möhler and T. Okada in Life Sciences, Vol. 20 2101-2110 (1977) the affinity of the test compounds for the $^3H$-diazepam receptor was quantitatively estimated by measuring the inhibition of specific $^3H$-diazepam binding to rat brain membranes by the tested compounds. The results obtained with some representative compounds of the present invention are summarized in Table V below.

In this table, inhibition is expressed in term of inhibitor constant $K_i$ which is defined as $K_i = IC_{50}/(1 + C/K_D)$ wherein $IC_{50}$ is the concentration of test substance required to displace 50 percent of the specific $^3H$-diazepam binding, C is $^3H$-diazepam concentration and $K_D$ is the affinity constant of $^3H$-diazepam for its receptor ($3.4 \times 10^{-9}M$).

Compounds with high affinity for the receptor will displace $^3H$-diazepam at low concentrations (low $IC_{50}$ values) and are therefore characterized by a low $K_i$. For better comprehension, the inhibitor constants of some known benzodiazepines are given below the dotted line in Table V.

TABLE V

| Compound of example No. | $K_i$ |
|---|---|
| 27 | $1.6 \times 10^{-8}$ |
| 29 | $2.8 \times 10^{-8}$ |
| 30 | $1.8 \times 10^{-8}$ |
| 31 | $1.7 \times 10^{-8}$ |

TABLE V-continued

| Compound of example No. | $K_i$ |
|---|---|
| 32 | $9.68 \times 10^{-10}$ |
| 35 | $4.6 \times 10^{-8}$ |
| 36 | $4.8 \times 10^{-8}$ |
| 41 | $2.1 \times 10^{-8}$ |
| 42 | $5.7 \times 10^{-8}$ |
| 43 | $1.6 \times 10^{-8}$ |
| 44 | $5.7 \times 10^{-8}$ |
| 45 | $3.2 \times 10^{-8}$ |
| 46 | $1.4 \times 10^{-8}$ |
| 47 | $3.9 \times 10^{-9}$ |
| 51 | $4.0 \times 10^{-8}$ |
| 64 | $2.0 \times 10^{-8}$ |
| 67 | $2.7 \times 10^{-9}$ |
| 72 | $1.5 \times 10^{-9}$ |
| 73 | $2.1 \times 10^{-7}$ |
| 74 | $1.7 \times 10^{-8}$ |
| 75 | $2.9 \times 10^{-8}$ |
| 79 | $2.7 \times 10^{-9}$ |
| 85 | $7.8 \times 10^{-9}$ |
| 101 | $2.9 \times 10^{-9}$ |
| 103 | $4.27 \times 10^{-10}$ |
| 104 | $8.06 \times 10^{-10}$ |
| 105 | $0.9 \times 10^{-9}$ |
| 107 | $5.65 \times 10^{-10}$ |
| 108 | $5.24 \times 10^{-10}$ |
| 112 | $6.0 \times 10^{-8}$ |
| Diazepam | $1.89 \times 10^{-9}$ |
| Oxazepam | $5.2 \times 10^{-9}$ |
| Flurazepam | $8.58 \times 10^{-9}$ |

Some of the compounds of the above list were also tested in vivo in those pharmacological tests thought to be predictive of anxiolytic activity in man. Classical pharmacological tests employed to confirm the antianxiety activity were the conditioned avoidance test and the antipentylenetetrazole test in mice. The conditioned avoidance test was carried out according to the method described by Cook and Weidley in Ann. N.Y. Acad. Sci. 1957, 66, 740, and subsequently modified by Maffii (J. Pharm. and Pharmacol., 1959, 11, 129-139). In this procedure a rat is placed in a chamber with a grid floor through which electric shocks may be delivered. This chamber is also equipped with a buzzer and with a wooden pole, electrically isolated, which is suspended from the top of the experimental chamber.

The animal soon learns to escape the shock by climbing the pole (unconditioned response—U.R.) and by climbing the pole in response to the buzzer alone (conditioned avoidance response—CR). After further exposure to the situation, the rat becomes conditioned and climbs the pole before the buzzer is activated; when this response becomes stable, the rat is considered to have developed a secondary conditioned response ($CR_2$).

The drug to be studied is then administered to these long-trained animals and its deconditioning effect is evaluated. In our experiments male rats of the CFHB Wistar strain, weighing 200-450 g were used, and it was found that doses of between about 1/30 and 1/10 of the corresponding $LD_{50}$s of the compounds of examples 30, 31, 45, 54, 67, 72, 73, 93, 95, 105, 112, and 114, when administered intraperitoneally, are effective in inhibiting the secondary conditioned response ($CR_2$), without influencing the primary conditioned and the unconditioned responses (CR and U.R.). Moreover, the activity of some of the compounds of the present invention has been tested in the antipentylenetetrazole test in mice. The experiments have been carried out by following essentially the methodology described by Berger in J. Pharm. Exptl. Ther. 104, 468, (1952). More particularly, a fatal dose of pentylenetetrazole (140 mg/kg s.c.) was administered to groups of ten mice each, 30 minutes after a selected dose of the potential anticonvulsant compound. One of these groups, the "control" group, did not receive the anticonvulsant but only the convulsant agent. Since the animals of the control group died within 30 minutes, the effectiveness of the compounds tested at each dose tested was expressed as the number of animals of the group which were still alive two hours after the administration of pentylenetetrazole, out of the total number of animals of the group (10).

The results obtained in these experiments are reported in Table VI below.

TABLE VI

| Compound of Example No. | $LD_{50}$ mg/kg i.p. | Dose (mg/kg i.p.) | Protected/treated |
|---|---|---|---|
| 31 | $\geq 300$ | 10 | 6/10 |
|  |  | 20 | 9/10 |
| 67 | $\geq 300$ | 5 | 4/10 |
|  |  | 10 | 8/10 |
| 105 | $\sim 500$ | 15 | 3/10 |
|  |  | 25 | 8/10 |

In view of the above, a further specific object of the present invention is the use of the compounds of the present invention as antianxiety agents.

With the term "use" it is intended to refer to all industrially applicable aspects and acts of said use, including the embodiment of the novel compounds into pharmaceutical compositions.

Suitable pharmaceutical compositions contain the novel compounds in admixture or conjunction with organic or inorganic, solid or liquid pharmaceutical excipients and may be employed for enteral or parenteral administration. Suitable excipients are substances that do not react with the new compounds such as for instance, water, gelatin, lactose, starches, magnesium stearate, talcum, vegetable oils, benzyl alcohol, polyalkylene glycols, or other known medicinal excipients. The new compounds may be administered by various routes: while the preferred route of administration is the oral one, intramuscular or intravenous administration can also be employed. For oral administration, the substances are compounded in such forms, as tablets, dispersible powders, capsules, granules, syrups, elixirs and solutions. For intraveneous or intramuscular administration the active ingredients are embodied into injectable dosage forms.

Such compositions are formulated as known in the art. The dosage regimen for the compounds of the present invention in accord with anti-anxiety treatment will depend upon a variety of factors including the particular compound used, the route of administration, and the type of treatment applied for. Good results can be obtained however by administering the compound of the present invention at a daily dosage range comprised between about 0.1 and about 2.0 g preferably administered in divided doses. It is however clear that a daily dosage beyond the above indicated range may also be employed depending on the individual conditions of the subject to be treated. Accordingly the present invention provides a therapeutic composition comprising from about 25 to about 250 mg of one of the compounds of the invention as the active ingredient together with a pharmaceutically acceptable carrier.

As an example, the active compounds of formula I can be formulated as in the following:

A capsule is prepared with

| | |
|---|---|
| 3-(4-methoxyphenyl)-6-(di(2-methoxyethyl)amine)-1,2,4-triazolo[3,4-a]phthalazine | 200 mg |
| Saccharose | 35 mg |
| Polyvinylpyrrolidone | 5 mg |
| Sodium dioctylsulfosuccinate | 1.8 mg |
| Magnesium stearate | 10 mg |
| Corn starch q.s. to | 300 mg |

A tablet is prepared with

| | |
|---|---|
| 6-(2-methoxyethoxy)-3-(4-methoxyphenyl)-1,2,4-triazolo[3,4-a]phthalazine | 150 mg |
| Saccharose | 30 mg |
| Polyvinylpyrrolidone | 5 mg |
| Sodium dioctylsulfosuccinate | 1.4 mg |
| Magnesium stearate | 8 mg |
| Corn starch q.s. to | 250 mg |

We claim:

1. A s-triazolo[3,4-a]phthalazine having the formula

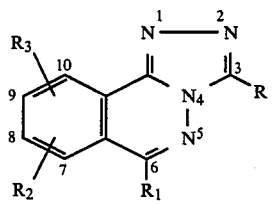

wherein

R represents phenyl, phenyl substituted with monohydroxy or from 1 to 3 substituents selected from $(C_1-C_6)$alkyl, $(C_1-C_6)$alkoxy, chloro, fluoro, bromo, phenyl, amino, mono- and di-$(C_1-C_4)$-alkylamino, $(C_2-C_4)$alkanoylamino, piperidino, cyano, nitro, trifluoromethyl, carboxy, and carbamyl with the proviso that the phenyl group cannot be substituted with mixtures of amino and nitro, alkanoylamino and alkylamino, or hydroxy and alkoxy groups, R is carbo$(C_1-C_4)$-alkoxy, chloro, $(C_1-C_4$alkylsulfinyl, $(C_1-C_4)$-alkylsulfonyl, a substituted amino group of the formula

wherein $R_4$ and $R_5$, each independently, represents $(C_1-C_4)$alkyl, $(C_2-C_4)$alkyl substituted with one or two groups independently selected from hydroxy, $(C_1-C_4)$alkoxy, halogen, carboxy, cyano, aminocarbonyl, mono- or di-$(C_1-C_4)$alkylaminocarbonyl, $(C_1-C_4)$alkoxycarbonyl, $(C_1-C_4)$alkoxythiocarbonyl and $(C_1-C_4)$alkyl-thiocarbonyl, or $R_4$ and $R_5$ independently are phenyl-$(C_1-C_4)$alkyl or substituted phenyl$(C_1-C_4)$alkyl wherein the alkyl portion as well as the phenyl portion may be substituted as defined above, or $R_4$ and $R_5$ taken together with the adjacent nitrogen atom may represent a saturated 4, 5 or 6-membered ring selected from the group consisting of azetidine, pyrrolidine, piperidine, piperazine and morpholine, and optionally bears one or two substituents independently seleted from $(C_1-C_4)$alkyl, phenyl, hydroxy, and carbo$(C_1-C_4$ alkoxy, or R represents an alkoxy or cycloalkoxy group of formula $-OR_6$ wherein $R_6$ stands for a $(C_1-C_6)$alkyl, substituted with one or two groups independently selected from hydroxy, amino, mono- or di-$(C_1-C_4)$alkylamino, $(C_1-C_4)$alkoxy, halogen, oxo, carboxy, aminocarbonyl, mono- or di-$(C_1-C_4)$alkylamino, $(C_1-C_4)$alkoxycarrbonyl, $(C_1-C_4)$alkoxythiocarbonyl and $(C_1-C_4)$alkylthiocarbonyl, or $R_6$ is a saturated 4, 5 or 6-membered ring selected from the group consisting of azetidine, pyrrolidine, piperidine, piperazine and morpholine, and optionally bears one or two substituents independently selected from $(C_1-C_4)$alkyl, phenyl, hydroxy, and carbo- $(C_1-C_4)$alkoxy, or $R_6$ is a $(C_5-C_8)$cycloalkyl group optionally substituted with one or more hydroxy and $(C_1-C_4)$alkoxy groups;

$R_1$ is selected from halogen, hydroxy, $(C_1-C_4)$alkylthio, $(C_1-C_4)$alkylsulfinyl, $(_1-C_4)$alkylsulfonyl, phenyl, phenyl substituted as above, a substituted amino group of the formula

wherein $R_7$ or $R_8$ are as defined above for $R_4$ and $R_5$, and an alkoxy or cycloalkoxy group of formula $-OR_9$ wherein $R_9$ is defined as $R_6$ above;

$R_2$ is hydrogen; and $R_3$ represents hydrogen, halogen, $(_1-C_4)$alkyl, $(C_1-C_6)$alkoxy and nitro; with the proviso that when $R_3$ is hydrogen and $R_1$ is chloro, R cannot be hydrogen, halogen, methyl, phenyl or 4-nitrophenyl, and that when $R_1$ is hydroxy, R must be different from phenyl; with the further proviso that when R and/or $R_1$ are $-OR_6$ or $-OR_9$, respectively, wherein the $R_6$ and/or $R_9$ are a saturated heterocyclic ring as above defined, the heteroatom of said heterocycle cannot be directly linked to the oxygen atom.

2. A compound as in claim 1 wherein R is phenyl or phenyl substituted as in claim 1, $R_1$ is an amino or substituted amino group of the formula

or an alkoxy or cycloalkoxy group of formula $-OR_9$ wherein $R_7$, $R_8$ and $R_9$ are as defined as in claim 1 and $R_2$ and $R_3$ each independently represent hydrogen, halogen, $)C_1-C_4)$alkyl and $C_1-C_4)$alkoxy.

3. A compound of claim 1 wherein $R_2$ and $R_3$ each independently represents hydrogen.

4. A compound of claim 1 or 3 wherein R represents phenyl or phenyl monosubstituted with an hydroxy, $(C_1-C_6)$alkyl, $(C_1-C_6)$alkoxy, chloro, fluoro, bromo, amino, or $(C_2-C_4)$alkanoylamino group.

5. A compound of claim 1, 3 or 4 wherein $R_1$ is a $(C_1-C_4)$alkylsulfonyl group, a substituted amino group of the formula

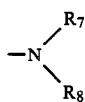

wherein $R_7$ and $R_8$ each independently represents a ($C_1$–$C_4$)alkyl or a ($C_2$–$C_4$)alkyl substituted with a group selected from hydroxy or ($C_1$–$C_4$)alkoxy or $R_7$ and $R_8$ taken together with the adjacent nitrogen atom represent an azetidine, pyrrolidine, piperidine, or morpholine each optionally substituted with one or two substituents independently selected from a ($C_1$–$C_4$)alkyl, hydroxy, or carbo($C_1$–$C_4$)alkoxy group.

6. A compound as in claim 1 which is 3-(4methoxyphenyl)-6-(di(2-methoxymethyl)amino)-1,2,4-triazolo[3,4-a]phthalazine.

7. A compound of claim 1 that is 3-phenyl-6-(1- pyrrolidinyl)-1,2,4-triázolo[3,4-a]phthalazine.

8. A compound of claim 1 that is N-(2-hydroxypropyl)-N- methyl-3-phenyl-1,2,4-triazolo[3,4-a]phthalazin-6-amine.

9. A compound of claim 1 that is 3-phenyl-6-morpholinyl-1,2,4-triazolo[3,4-a]phthalazine.

10. A compound of claim 1 that is N-(2-hydroxypropyl)-3-(4-methoxyphenyl)-N-methyl-1,2,4-triazolo[3,4-a]phthalazin-6- amine.

11. A compound of claim 1 that is N-(3-hydroxypropyl)-3-(4-methoxyphenyl)-N-methyl-1,2,4-triazolo[3,4-a]phthalazin-6- amine.

12. A compound of claim 1 that is 3-phenyl-N,N-dimethyl-1,2,4-triazolo[3,4-a]phthalazin-6-amine.

13. A compound of claim 1 that is 3-phenyl-N,N-diethyl- 1,2,4-triazolo[3,4-a]phthalazin-6-amine.

14. A compound of claim 1 that is 3-phenyl-6-piperidinyl-1,2,4-triazolo[3,4-a]phthalazine.

15. A compound of claim 1 that is 3-phenyl-6-(3,3-dimethyl-1-azetidinyl)-1,2,4-triazolo[3,4-a]phthalazine.

16. A compound of claim 1 that is N-ethyl-N-methyl-3- phenyl-1,2,4-triazolo[3,4-a]phthalazin-6-amine.

17. A compound of claim 1 that is 3-phenyl-6-(1-pyrrolidinyl)-1,2,4-triazolo[3,4-a]phthalazine.

18. A compound of claim 1 that is 3-(4-acetylaminophenyl)- 6-(1-pyrrolidinyl)-1,2,4-triazolo[3,4-a]phthalazine.

19. A compound of claim 1 that is 3-(4-fluorophenyl)-6-(1- pyrrolidinyl)-1,2,4-triazolo[3,4-a]phthalazine.

20. A compound of claim 1 that is 1-3-(4-methoxyphenyl)-1,2,4-triazolo[3,4-a]phthalazin-6-yl]-4-piperazinecarboxylic acid ethyl ester.

21. A compound of claim 1 that is 3-phenyl-6-(3,5-dimethyl-1-piperidinyl)-1,2,4-triazolo[3,4-a]phthalazine.

22. A compound of claim 1 that is 3-(4-hydroxyphenyl)-6-(1-pyrrolidinyl)-1,2,4triazolo[3,4-a]phthalazine.

23. A compound of claim 1 that is 3-(4-aminophenyl)-6-(1- pyrrolidinyl)-1,2,4-triazolo[3,4-a]phthalazine.

24. a compound of claim 1 that is 3-(4-methoxyphenyl)-6-(3-hydroxy-1-pyrrolidinyl)-1,2,4-triazolo[3,4-a]phthalazine.

25. A compound of claim 1 that is 6-ethoxy-3-phenyl-1,2,4-triazolo [3,4-a]phthalazine.

26. A compound of claim 1 that is 6-ethoxy-3-(4-methoxyphenyl)-1,2,4-triazolo[3,4-a]phthalazine.

27. A compound of claim 1 that is 6-ethylsulfonyl-3-phenyl-1,2,4-triazolo[3,4-a]phthalazine.

28. An antianxiety composition having an effective amount of a compound of claim 1 as the active ingredient in admixture with a pharmaceutically acceptable carrier.

29. An antianxiety composition as in claim 28 having from 25 to 250 mg of a compound of claim 1 per dosage unit form.

* * * * *

UNITED STATES PATENT AND TRADEMARK OFFICE
CERTIFICATE OF CORRECTION

PATENT NO. : 4,788,186

DATED : November 29, 1988

INVENTOR(S) : Emilio Ocelli et al.

It is certified that error appears in the above-identified patent and that said Letters Patent is hereby corrected as shown below:

At column 3, line 7, the patent reads "sedation, motor incohordination, etc." and should read --sedation, loss of motor coordination, etc.--. At column 3, line 25, the patent reads "synthetized" and should read --synthesized--. At column 4, line 38, the patent reads "thiolo" and should read --thiol--. At column 5, line 23, the patent reads "(Cl $_{1C-4}$) and should read --$(C_1-C_4)$--. At column 7, line 64, the patent reads "($C_1-C_6$alkyl" and should read --$(C_1-C_6)$alkyl--. At column 12, line 56, the patent reads "vessell" and should read --vessel--. At column 24, lines 57-58, the patent reads "chloro-triazolo±1,2,4-triazolo[3,4-a]pthalazine" and should read --chloro-triazolo[3,4-a]pthalazine--. At column 24, lines 66-67, the patent reads "pthalazinens" and should read --pthalazines--. At column 28, line 11, the patent reads "6-thiolo" and should read --6-thiol--. At column 28, lines 46 and 59, the patent reads "3-thiolo" and should read --3-thiol--. At column 29, lines 30, 50 and 57, the patent reads "3-thiolo" and should read --3-thiol--. At column 30, line 66 and at column 31, line 10, the patent reads "isobutyrroyl" and should read --isobutyroyl--. At column 31, lines 33 and 51, the patent reads "3-thiolo" and should read --3-thiol--. At column 32, line 42, the patent reads "[[/3-" and should read -- [[3- --. At column 34, line 7, the patent reads "etanol" and should read --ethanol--. At column 34, lines 15-16, the patent reads "drypped into the water so as to held" and should read --dripped into the water so as to hold--.
At column 37, line 43, the patent reads "($C_1-C_4$alkylsulfinyl," and should read --$(C_1-C_4)$alkylsulfinyl,--.

UNITED STATES PATENT AND TRADEMARK OFFICE
CERTIFICATE OF CORRECTION

PATENT NO. : 4,788,186

DATED : November 29, 1988

INVENTOR(S) : Emilio Ocelli et al.

It is certified that error appears in the above-identified patent and that said Letters Patent is hereby corrected as shown below:

At column 38, claim 1, line 7, the patent reads "alkoxycarrbonyl" and should read --alkoxycarbonyl-- At column 38, claim 1, line 20, the patent reads "$(_1-C_4)$" and should read --$(C_1-C_4)$--. At column 38, claim 1, line 32, the patent reads "is defined" and should read --is as defined--. At column 38, claim 1, line 34, the patent reads "$(_1-C_4)$" and should read --$(C_1-C_4)$--. At column 38, claim 2, line 58, the patent reads ")$C_1-C_4$)alkyl and $C_1-C_4$)alkoxy." and should read --$(C_1-C_4$alkyl and $(C_1-C_4)$alkoxy.--. At column 39, claim 6, lines 15-16, the patent reads "(4methoxyphenyl)-6-(di(2-methoxymethyl)" and should read --(4-methoxyphenyl)-6-(di-2-methoxyethyl)--. At column 40, claim 22, line 18, the patent reads "1,2,4triazolo" and should read --1,2,4-triazolo--.

Signed and Sealed this

Sixteenth Day of May, 1989

Attest:

DONALD J. QUIGG

Attesting Officer

Commissioner of Patents and Trademarks